United States Patent
Miura et al.

[11] Patent Number: 6,154,667
[45] Date of Patent: Nov. 28, 2000

[54] PULSE OXIMETER PROBE

[75] Inventors: Hiroko Miura; Noriaki Todokoro; Hideo Ozawa, all of Tokyo, Japan

[73] Assignee: Nihon Kohden Corporation, Tokyo, Japan

[21] Appl. No.: 09/222,312

[22] Filed: Dec. 28, 1998

[30] Foreign Application Priority Data

Dec. 26, 1997 [JP] Japan .................................... 9-359935

[51] Int. Cl.⁷ ....................................................... A61B 5/00
[52] U.S. Cl. ............................................ 600/323; 600/344
[58] Field of Search ................................... 600/310, 322, 600/323, 340, 344, 473, 476

[56] References Cited

U.S. PATENT DOCUMENTS

| | | | |
|---|---|---|---|
| 4,334,544 | 6/1982 | Hill et al. ................................. | 600/473 |
| 4,685,464 | 8/1987 | Goldberger et al. . | |
| 5,247,931 | 9/1993 | Norwood ................................. | 600/344 |
| 5,339,810 | 8/1994 | Ivers et al. . | |
| 5,372,134 | 12/1994 | Richardson ............................. | 600/323 |
| 5,437,275 | 8/1995 | Amundsen et al. ..................... | 600/323 |
| 5,438,986 | 8/1995 | Disch et al. . | |
| 5,490,523 | 2/1996 | Isaacson et al. . | |
| 5,551,423 | 9/1996 | Sugiura ................................... | 600/323 |
| 5,619,992 | 4/1997 | Guthrie et al. .......................... | 600/310 |
| 5,676,139 | 10/1997 | Goldberger et al. . | |
| 5,788,634 | 8/1998 | Suda et al. .............................. | 600/476 |
| 5,792,052 | 8/1998 | Isaacson et al. ........................ | 600/323 |
| 5,810,724 | 9/1998 | Gronvall ................................. | 600/323 |

*Primary Examiner*—Eric F. Winakur
*Assistant Examiner*—Joseph A. Cadugan
*Attorney, Agent, or Firm*—Sughrue, Mion, Zinn, Macpeak & Seas, PLLC

[57] ABSTRACT

A movable mechanism (3) moves a first housing (1) having a light emitting element (4) mounted thereon and a second housing (2) having a photo sensing element (5) mounted thereon in a state that those housings are parallel to each other. The movable mechanism (3) includes a pair of knobs (15A and 15B) and a spring (11) urging those knobs to move apart from each other. When the knobs (15A and 15B), while resisting the force of the spring (11), are pressed so as to make a mutual approach of those knobs, the first housing (1) and the second housing (2) are moved apart from each other. At this time, a finger of a patient is placed between the housings, and an operator gradually lessens his force applied to the knobs (15A and 15B) and reduces the force to zero. Then, the finger is held between the first housing (1) and the second housing (2). In this case, the orientations of the axes of the light emitting element (4) and the photo sensing element (5) are variable irrespective of the thickness of the finger.

6 Claims, 11 Drawing Sheets

PRIOR ART

PULSE OXIMETER PROBE

BACKGROUND OF THE INVENTION

1. Field of the Invention

The present invention relates to a probe in use with a pulse oximeter which measures an arterial blood oxygen saturation of a patient in a state that the probe is attached to a finger, toe or earlobe of the patient.

2. Related Art

Figure 14:
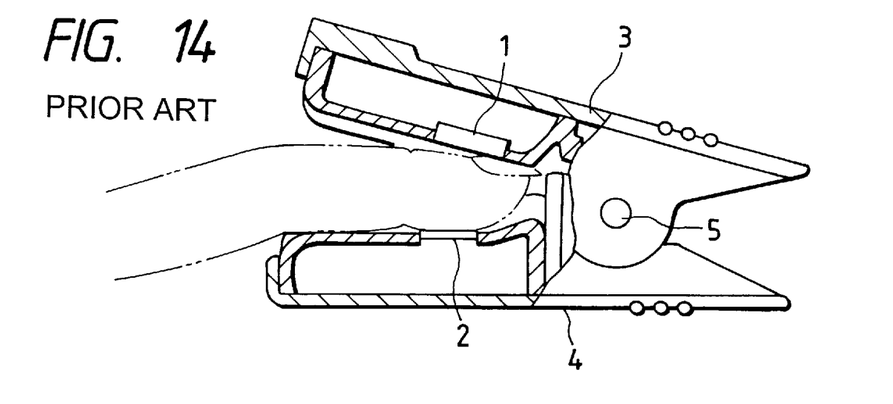
FIG. 14 is a view showing a conventional probe in use with a pulse oximeter.

A known probe of this type has a structure as shown in FIG. 14. A light emitting element 51 and a photo sensing element 52 are mounted on housings 53 and 54, respectively. The housings 53 and 54 may be turned about a shaft 55. The light emitting element 51 and the photo sensing element 52 are urged, by a spring (not shown), so as to be biased toward each other. The example illustrated is a probe designed so as to be attached to a finger of a patient or subject. In use, as shown in FIG. 14, the finger is inserted into a space and held between the housings 53 and 54.

The probe thus designed is advantageous in that its structure is simple and it is easy to the patient's finger to and remove it from the probe. However, the probe has the following disadvantages. In a case where what is to be set to the probe has a large individual variations, such as the finger, it is difficult for one probe to properly receive every sized finger for measurement. For example, the probe cannot properly receive the finger having a thickness of a predetermined value or larger. In this case, the finger, when set to the probe, is likely to shift from a correct position between the housings or to slip off. Further, an angle between the housings varies with the thickness of the finger inserted therebetween. Therefore, the optical axis of the light emitting element is misaligned with that of the photo sensing element. As a result, the measurement by the probe is instable.

SUMMARY OF THE INVENTION

Accordingly, an object of the present invention is to provide a probe in use with a pulse oximeter which stably measures an arterial blood oxygen saturation of a patient without any misalignment of the optical axes of the light emitting and sensing elements.

According to the present invention, there is provided a probe for use in emitting a patient tissue to measure blood constituent. The probe includes:

a first housing;

a second housing and;

a light emitting element disposed on one of the first and second housing.

A photo sensing element is provided for sensing light emitted from the light emitting element disposed on one of the first and second housing;

a movable mechanism having a pair of knobs, is operable so that when the paired knobs are moved to each other, the movable mechanism moves the housing apart from the each other in a state that the housings are parallel to each other. When the paired knobs are moved apart from each other, the movable mechanism moves the housings in the directions in which the housings move to each other; and an elastic member is provided for urging the pair of knobs to be separated from each other.

To use the thus constructed probe, an operator presses the paired knobs in the directions of making a mutual approach of the knobs; the movable mechanism moves the housings apart from each other; the operator places a biomedical tissue between the housings; gradually lessens the pressure applied to the knobs and detaches his fingers from the knobs; and the elastic member automatically sets the biomedical tissue between the housings in a state the pair of housings are parallel to each other.

There is another probe in use with a pulse oximeter, which has the same construction as that of the above-mentioned first probe, and has another unique construction. The probe, when used, is attached to a finger of a subject; and the movable mechanism is arranged to form a gap so as to allow one of the pair of housings to be tiltable with respect to the other.

In the improved probe, when the finger is held between the pair of housings, the finger is put on the housings in a well fitting manner, and one of the paired housings is slanted to the other.

There is a further probe in use with a pulse oximeter, which has the same construction as that of the first probe, and has a unique construction. The lead wires connected to the light emitting element and the photo sensing element are respectively led out of the ends of the pair of housings; the probe further includes a wire holder consisting of two tubes through which the lead wires are inserted respectively. The tubes are separated from each other at one end of the wire holder while the tubes are bonded together at the other end. When the pair of housings are attached to an earlobe of the subject, the wire holder is put on the earlobe and the lead wires are laid along the obverse and reverse side of the earlobe.

In attaching the thus constructed probe to the earlobe, the wire holder is set to the earlobe, and the housings receive lessened force from the lead wires. The result is that the probe hardly detaches from the earlobe.

DETAILED DESCRIPTION OF THE PREFERRED EMBODIMENTS

Figure 1:
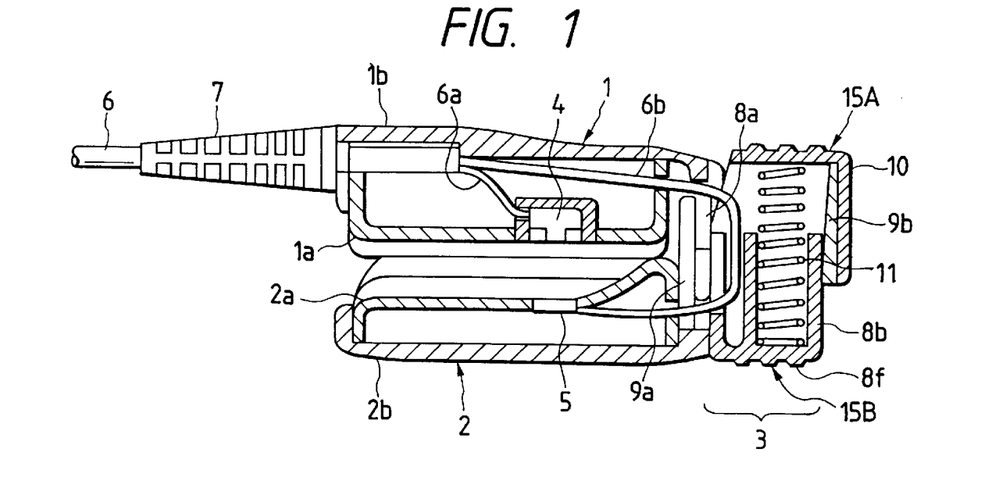
FIG. 1 is a longitudinal sectional view showing a probe in use with a pulse oximeter which is a first embodiment of the present invention.
Figure 2:
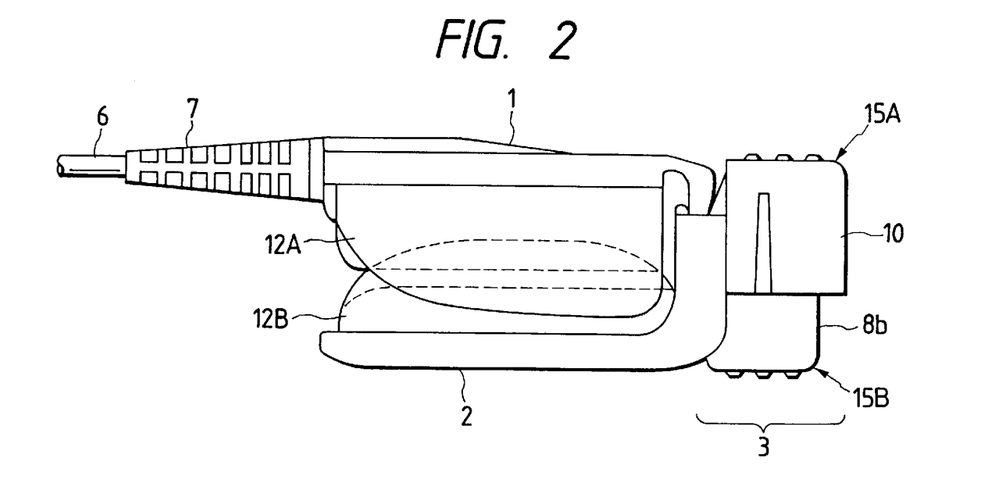
FIG. 2 is a side view showing the probe of FIG. 1.

FIG. 1 is a longitudinal sectional view showing a probe in use with a pulse oximeter which is a first embodiment of the present invention. The pulse oximeter probe, when used, is attached to a finger of a patient. An external appearance of the probe is shown in FIG. 2. As shown, the probe is made up of a first housing 1, a second housing 2, and a movable mechanism 3 for moving those housings to each other and the housings apart from each other. The first housing 1 includes a first optical-element holder 1a and a first housing base 1b. The first optical-element holder 1a has a recess which is longitudinally extended and shaped so as to secure a well fitting of the back of a finger when it receives the finger, and a light emitting element 4 located at the middle part of the recess. The first housing base 1b supports the first optical-element holder 1a. The second housing 2 includes a second optical-element holder 2a and a second housing base 2b. The second optical-element holder 2a has a recess which is longitudinally extended and shaped so as to secure a well fitting of the inner surface of a finger when it receives the finger, and a photo sensing element 5 located at the middle part of the recess. The second housing base 2b supports the second optical-element holder 2a. A lead wire 6a, which is connected at one end to the light emitting element 4 within the first housing 1, is led outside out of the first housing 1. A lead wire 6b, which is connected at one end to the photo sensing element 5 within the second housing 2, is led out of the second housing and guided to the exterior by way of the movable mechanism 3 and the first housing 1. Specifically, the lead wires 6a and 6b are coupled together into a lead wire 6 within the first housing 1, and guided to the exterior through an elastic tubular member 7 attached to one end of the first housing 1, which is opposite to the other end thereof coupled with the movable mechanism 3. The elastic tubular member 7 is provided for preventing the lead wire 6 from being damaged when it is bent.

Figure 3:
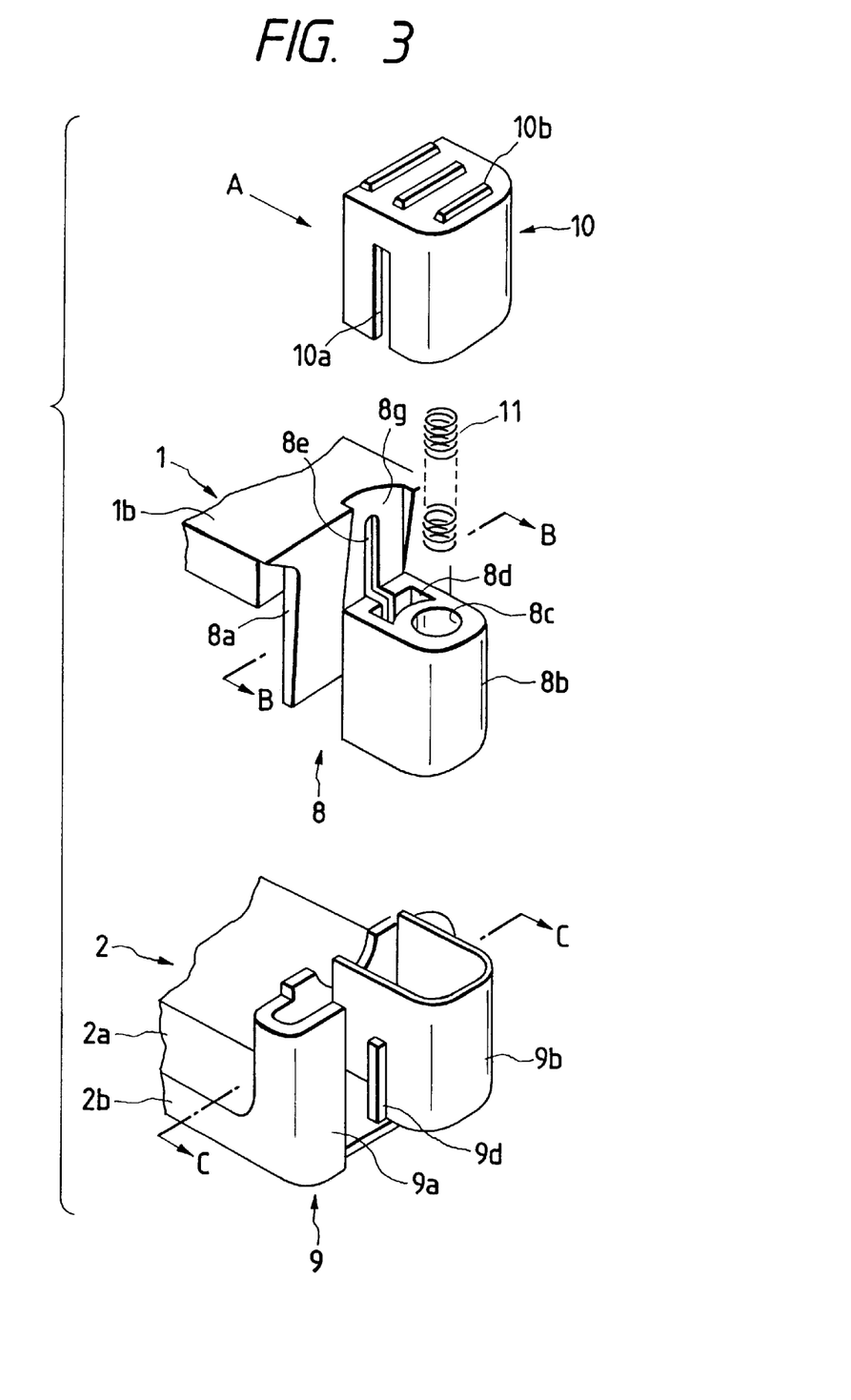
FIG. 3 is an exploded view showing a movable mechanism 3 of the probe of FIG. 1.

The movable mechanism 3 will be described hereinafter. An exploded view of the movable mechanism 3 is shown in FIG. 3. The portions of the movable mechanism 3, when viewed in the directions of arrows A, B and C, are illustrated in FIG. 4.

Figure 4A:
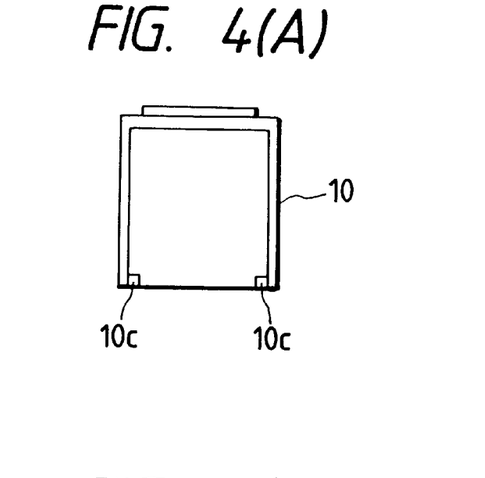
FIG. 4 is a view showing the portions of the probe when viewed in the directions of arrows A, B and C in FIG. 3.
Figure 4B:
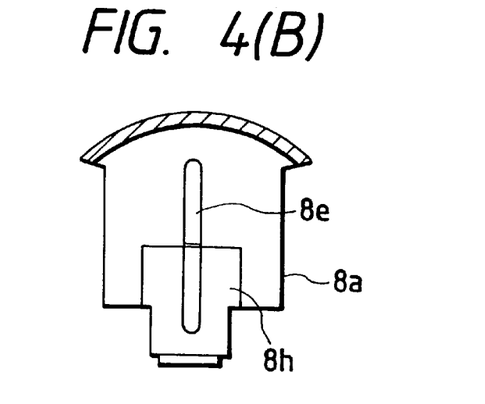

As shown, a slide assembly 8 is provided at one end of the first housing base 1b of the first housing 1. The slide assembly 8 includes a slide plate 8a which is extended in a direction substantially orthogonal to the longitudinal direction of the first housing base 1b, and a slide block 8b which is provided on the rear side of the slide plate 8a while ranging from a mid position of the rear side to a lower position. The slide block 8b is narrower than the slide plate 8a and its lower end is located below the lower end of the slide plate 8a. A spring holder 8c and a lead-wire holder 8d are formed in the slide block 8b, while both ranging from the upper surface of the slide block to the lower part thereof. The spring holder 8c holds a spring 11 therein. A slit 8e continuously ranges from the slide plate 8a to the slide block 8b as shown in FIG. 4(B). The lead-wire holder 8d communicates with a space partially defined by the front side of the slide plate 8a through the slit 8e. The rear side of the slide plate 8a slants to the rear side in a region ranging from a position just above the slide block 8b to the top of the slide plate 8a, whereby a recess 8g is formed in the region of the rear side of the slide plate 8a. A recess 8h is formed in the front side while extending to an area thereof corresponding in location to the slide block 8b. Protrusions 8f are provided on the lower surface of the slide block 8b for the antiskid purpose (FIG. 1). The first housing base 1b, the slide plate 8a and the slide block 8b are molded into one piece.

Figure 4C:
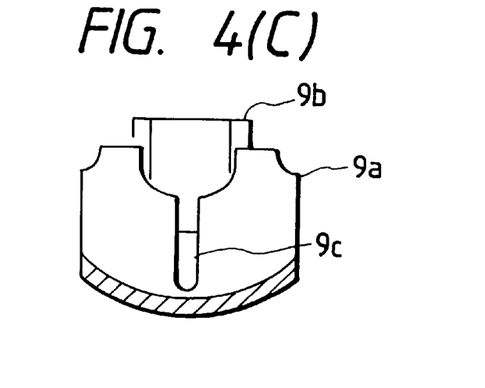

A slide holder 9 is provided at one end of the second housing base 2b of the second housing 2. The slide holder 9 includes a slide-plate holder 9a and a slide-block holder 9b, both standing erect with respect to the longitudinal direction of the second housing base 2b. The slide-plate holder 9a holds the slide plate 8a of the slide assembly 8, and the slide-block holder 9b holds the slide block 8b of the slide assembly 8. The rear wall of the slide-block holder 9b, as shown in FIG. 1, becomes thin toward its top. The inner wall of the slide-plate holder 9a, as shown in FIG. 4(C), is vertically cut long at a mid position of the inner wall of the slide-plate holder 9a, to form a slit 9c. Guide bars 9d, square in cross section, are vertically provided on both side walls of the slide-block holder 9b, respectively. When a cover 10 is put on the slide holder 9, the guide bars 9d of slide-block holder 9b are respectively inserted into slits 10a which are formed in both side walls of the cover 10. Long narrow protrusions 10b are formed on the upper surface of the cover 10, for the antiskid purpose. As shown in FIG. 4(A), the front side and the bottom of the cover 10 are opened. Protrusions 10c are provided at the positions of the lower corners of the cover 10, which are closer to the front opening of the cover than the slits 10a. The protrusions 10c are used for fixing the cover 10 to the slide-block holder 9b when the cover 10 is put on the slide holder 9. The second housing base 2b and the slide holder 9 are formed by one-piece molding.

The movable mechanism 3 is thus constructed. The assembling of the movable mechanism 3 will be described hereunder. To begin with, the slide assembly 8 integrally coupled with the first housing base 1b of the first housing 1 is inserted into the slide holder 9 integrally coupled with the first housing base 1b. Specifically, the slide plate 8a is inserted into the slide-plate holder 9a, and the slide block 8b is inserted into the slide-block holder 9b. Then, the spring 11 is inserted into the spring holder 8c of the slide assembly 8; the cover 10 is put on the slide-block holder 9b while pressing the spring 11 in the spring holder 8c; the protrusions 10c of the cover 10 are inserted into the guide bars 9d of the slide holder 9; and the cover 10 is pressed down till the lower end of the cover 10 reaches the lower end of the slide-block holder 9b. The protrusions 10c of the cover 10 are brought into contact with the lower corners of the slide-block holder 9b, respectively, to complete the attaching of the cover 10 to the slide-block holder 9b. The combination of the cover 10 and the slide-block holder 9b, and the slide block 8b form a pair of knobs 15A and 15B. A state of the probe under discussion is as shown in FIG. 1 when no force is externally applied to the knobs 15A and 15B.

In the movable mechanism 3 thus constructed, the slit 8e of the slide assembly 8 is aligned with the slit 9c of the slide holder 9 to form a composite slit. The lead wire 6b may be laid such that it is derived from the photo sensing element 5 within the second housing 2 and guided to the interior of the second housing 2 by way of a route of the composite slit and the lead-wire holder 8d of the movable mechanism 3. With this structure, the lead wire 6b does not interrupt the mutual motions of the first housing 1 and the second housing 2 in any way.

As shown in FIG. 2, shield plates 12A and 12B are respectively provided on the side walls of the first housing base 1b and the second housing base 2b in order to shut off external light going to the inside of the probe.

Figure 5A:
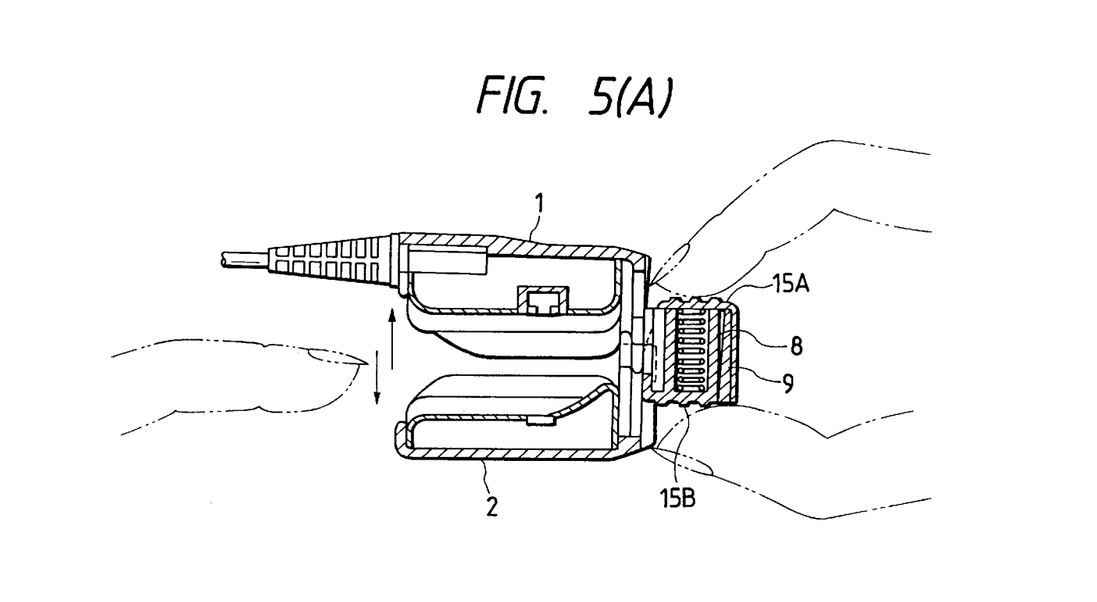
FIG. 5(A) and FIG. 5(B) are diagrams useful in explaining the operation of the FIG. 1 probe.
Figure 5B:
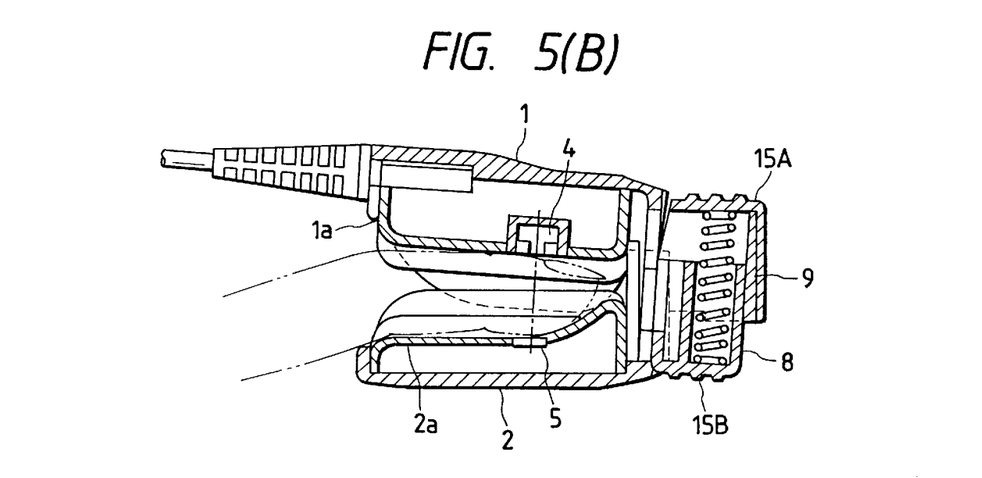

How to use the probe thus constructed and assembled will be described with reference to FIG. 5. An operator holds the paired knobs 15A and 15B between his fingers to move these knobs to each other. The slide assembly 8 slidably moves with respect to the slide holder 9, and the first housing 1 and the second housing 2 move away from each other while being parallel to each other. The operator guides the patient's finger into a space between the first housing 1 and the second housing 2; gradually decreases his force applied to the paired knobs 15A and 15B; and the patient's finger is brought, by the spring 11 force, into close contact with the first optical-element holder 1a and the second optical-element holder 2a, viz., it is compressed between the first housing 1 and the second housing 2. This state of the probe is illustrated in FIG. 5(B). When the probe is applied to the finger as shown, the optical axis of the light emitting element 4 is substantially coincident with that of the photo sensing element 5.

Figure 6:
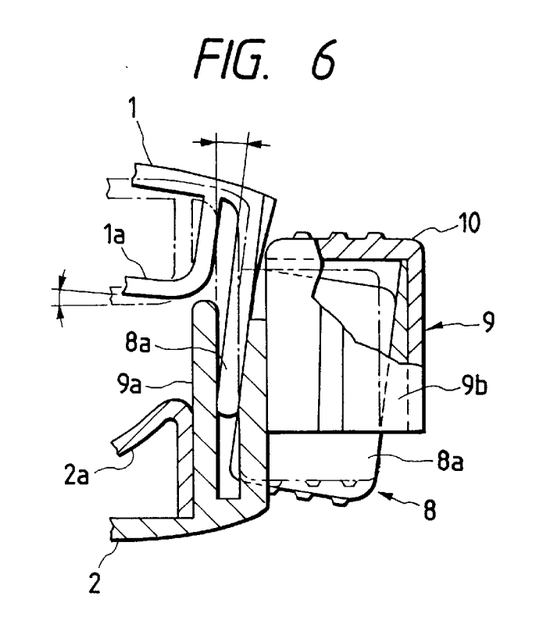
FIG. 6 is another diagram useful in explaining the operation of the FIG. 1 probe.

In this embodiment, as shown in FIG. 6, a gap is provided between the slide assembly 8 and the slide holder 9: a gap is present between the slide plate 8a and the slide-plate holder 9a, and a gap is present between the slide block 8b and the slide-block holder 9b. With the presence of the gap, when the patient's finger is compressed between the first housing 1 and the second housing 2, the slide assembly 8 is slightly slanted with respect to the slide holder 9 as indicated by arrows. For this reason, the first optical-element holder 1a and the second optical-element holder 2a are properly angled with respect to the finger so as to be brought into close contact with the finger. At this time, as indicated by circle marks in FIG. 6, the front side of the slide plate 8a comes in contact with the inner wall of the slide-plate holder 9a. Therefore, once the finger is inserted between the first housing 1 and the second housing 2 and nipped therewith, if the finger moves therebetween, there is no chance of further opening of those housings unless the operator compresses the knobs 15A and 15B.

Figure 7A:
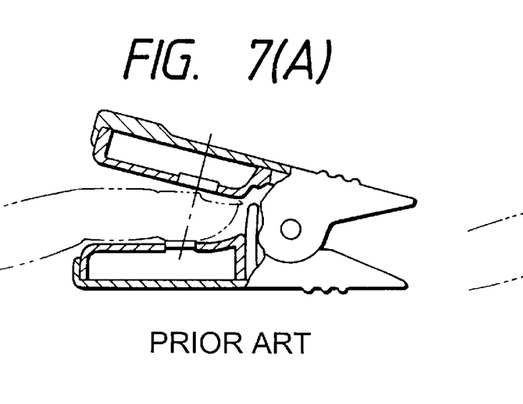
FIGS. 7(a) and 7(b) are diagrams comparatively showing a state of the FIG. 1 probe when it applied to the patient's finger and a state of the conventional probe when so done.
Figure 7B:
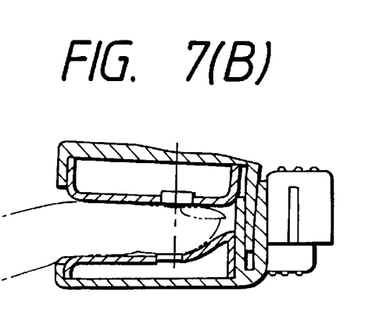

FIGS. 7 (A) and (B) are diagrams comparatively showing a state of the conventional probe and the present invention probe when applied to a patient's finger. FIG. 7 (A) shows the conventional probe, and FIG. 7 (B) shows the probe of the present invention. As seen, the optical axes of the light emitting and sensing elements vary in their orientations with the thickness of the finger in the conventional probe, while the optical axes of those optical elements substantially coincide in their orientations with the finger thickness.

Figure 10:
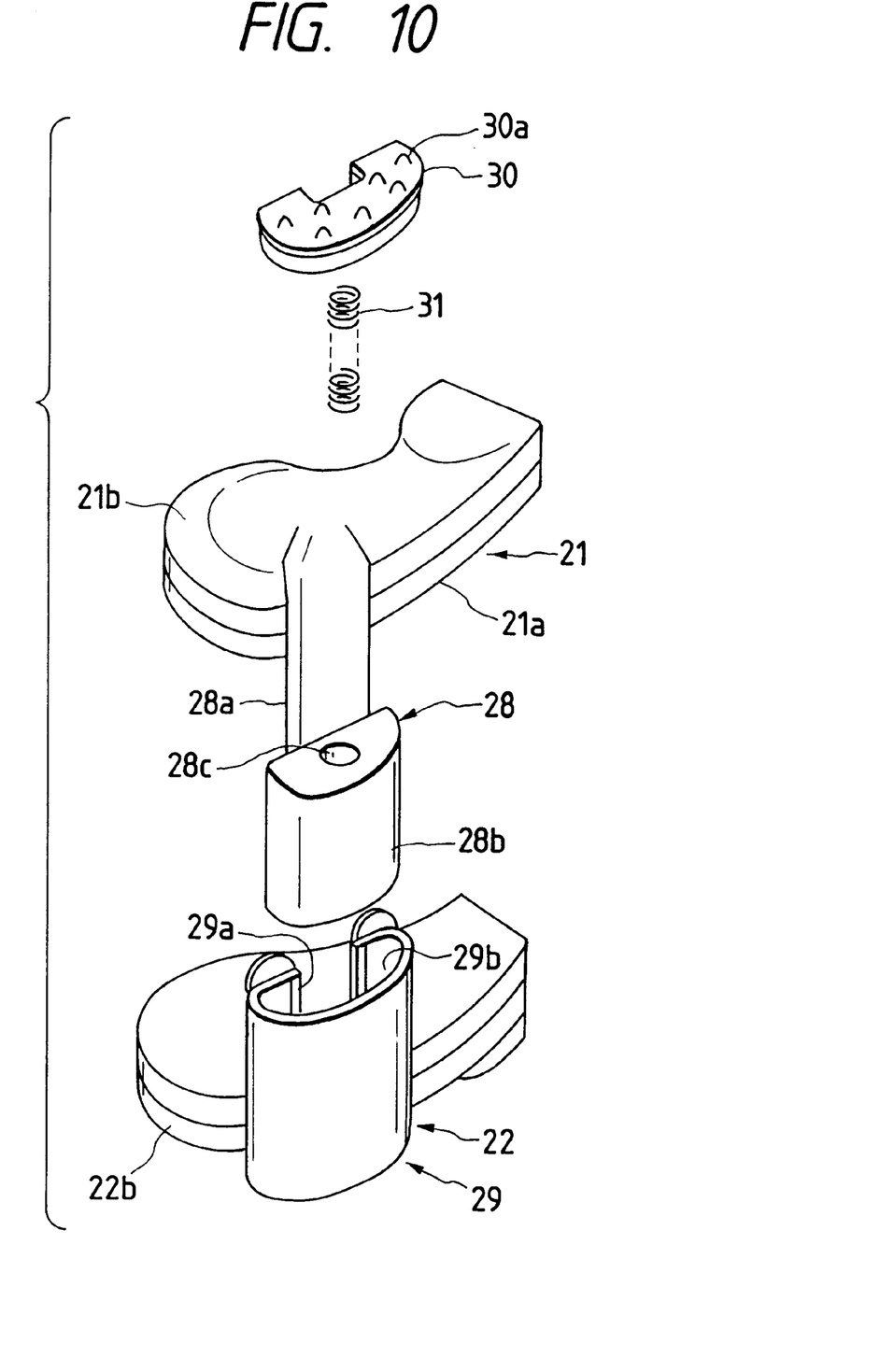
FIG. 10 is an exploded view showing the FIG. 8 probe.

A probe in use with a pulse oximeter which is a second embodiment of the invention will be described with reference to FIGS. 8 through 13. The pulse oximeter probe is attached to an earlobe of a patient. FIGS. 9 (A) to (D) show external appearances of the pulse oximeter probe; FIGS. 9(A) to 9(D) are a left side view, a front view, a right side view, and a plan view of the pulse oximeter probe. FIG. 10 shows an exploded view of the probe. As shown, the probe is made up of a first housing 21, a second housing 22, and a movable mechanism 23 for moving those housings to each other and the housings apart from each other. The first housing 21 includes a first optical-element holder 21a for holding a light emitting element 24 at the middle position thereof, and a first housing base 21b for supporting the first optical-element holder 21a. The second housing 22 includes a second optical-element holder 22a for holding a photo sensing element 25 at the middle position thereof, and a second housing base 22b for supporting the second optical-element holder 22a. A lead wire 26a, which is connected at one end to the light emitting element 24 within the first housing 21, is led outside out of the first housing 21. A lead wire 26b, which is connected at one end to the photo sensing element 25 within the second housing 22, is led outside out of the second housing. Elastic tubular members 27a and 27b are provided for preventing the lead wires 26a and 26b from being damaged when those are bent.

The movable mechanism 23 will be described with reference to FIG. 10. As shown, the first housing base 21b of the first housing 21 is provided with a slide assembly 28. The slide assembly 28 includes a slide plate 28a and a slide block 28b. The slide plate 28a is disposed substantially orthogonal to the element mounting surface of the first optical-element holder 21a with the light emitting element 24 mounted thereon. The slide block 28b is extended downward from a mid position of the slide plate 28a. The slide block 28b is bored thereinto from its top surface to form a spring holder 28c. A coiled spring 31 is put into the spring holder 28c.

Figure 8:
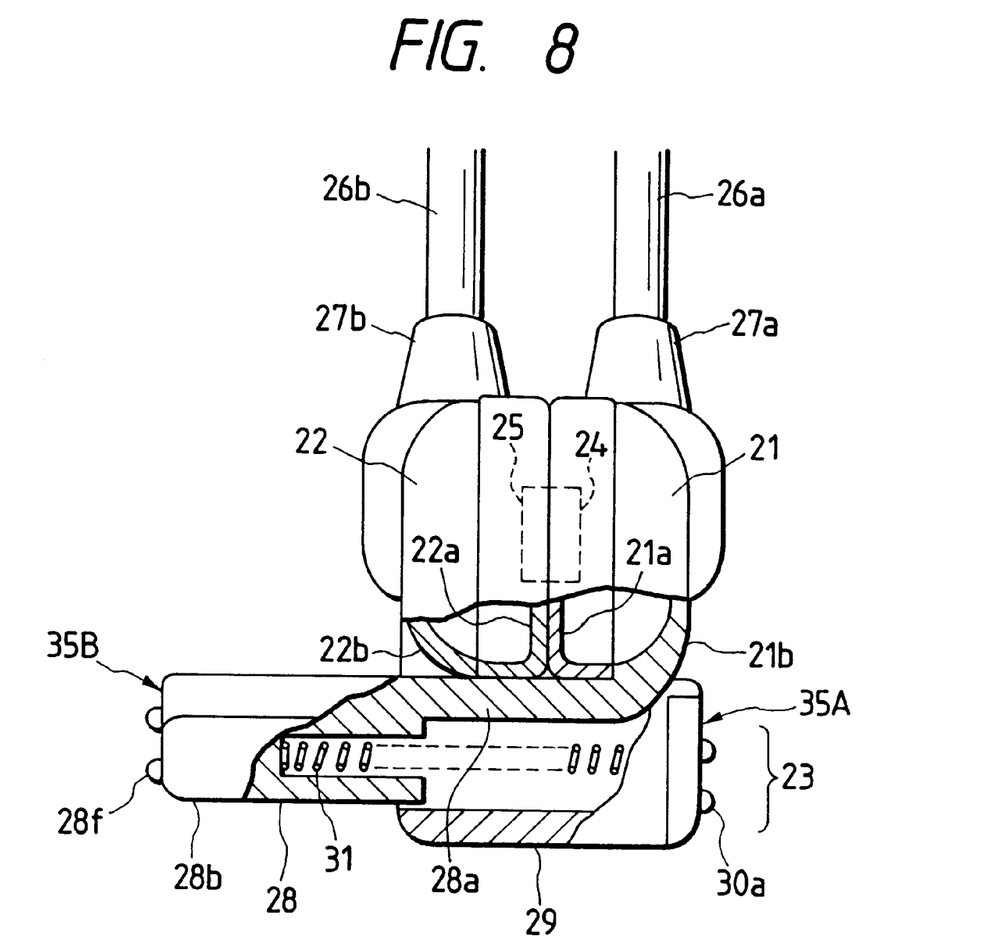
FIG. 8 is a view, partly broken, showing a probe in use with a pulse oximeter which is a second embodiment of the present invention.
Figure 9A:
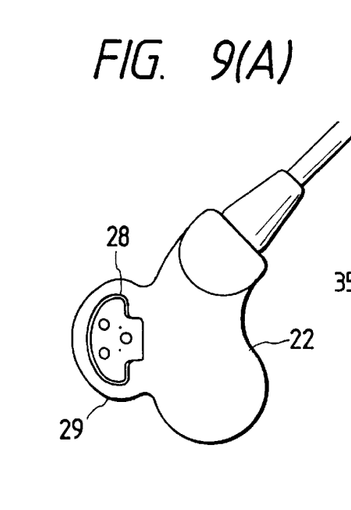
FIGS. 9(A)–9(D) are views showing an external appearance of the FIG. 8 probe.
Figure 9B:
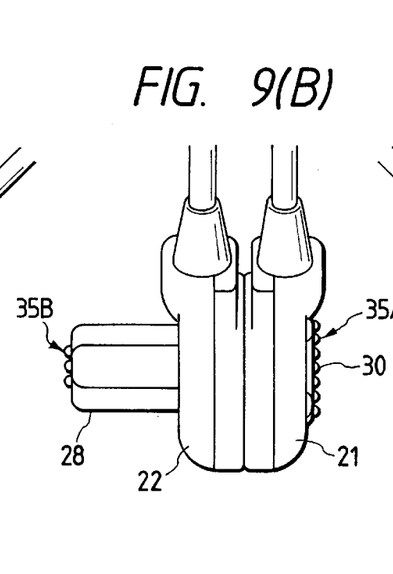
Figure 9C:
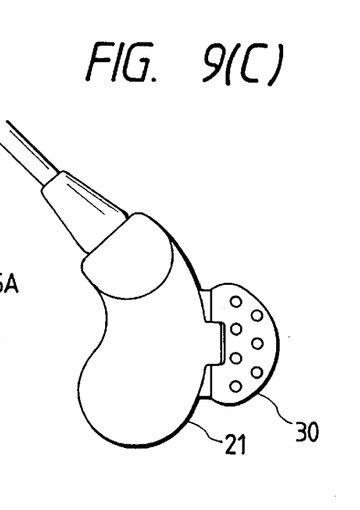
Figure 9D:
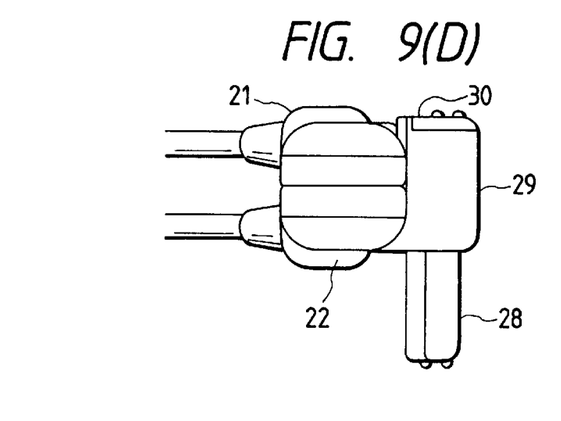

As shown in FIG. 8, a plural number of antiskid protrusions 28f are provided on the lower surface of the slide block 28b. The first housing base 21b, the slide plate 28a and the slide block 28b are formed by one-piece molding.

The second housing base 22b of the second housing 22 is provided with a slide holder 29. The slide holder 29 includes a slide-plate holder 29a and a slide-block holder 29b. The slide-plate holder 29a is disposed substantially orthogonal to the element mounting surface of the second optical-element holder 22a with the photo sensing element 25 mounted thereon. The slide-plate holder 29a holds the slide plate 28a of the slide assembly 28, and the slide-block holder 29b holds the slide block 28b of the slide assembly 28. A cover 30 is put on the top of the slide holder 29 to cover the opening of the top thereof.

A plural number of antiskid protrusions 30a are formed on the upper surface of the cover 30.

The assembling of the movable mechanism 23 thus constructed will be described. The slide assembly 28 coupled to the first housing base 21b is inserted into the slide holder 29 coupled to the second housing base 22b: the slide plate 28a is inserted into the slide-plate holder 29a, and the slide block 28b is inserted into the slide-block holder 29b. The coiled spring 31 is inserted into the spring holder 28c; the cover 30 is put on the top of the slide-block holder 29b while pressing the coiled spring 31; and fastened to the slide-block holder 29b. The combination of the cover 30 and the slide-block holder 29b, and the slide block 28b form a pair of knobs 35A and 35B. A state of the probe when no force is externally applied to the knobs 35A and 35B is as shown in FIGS. 8 and 9.

Figure 13:
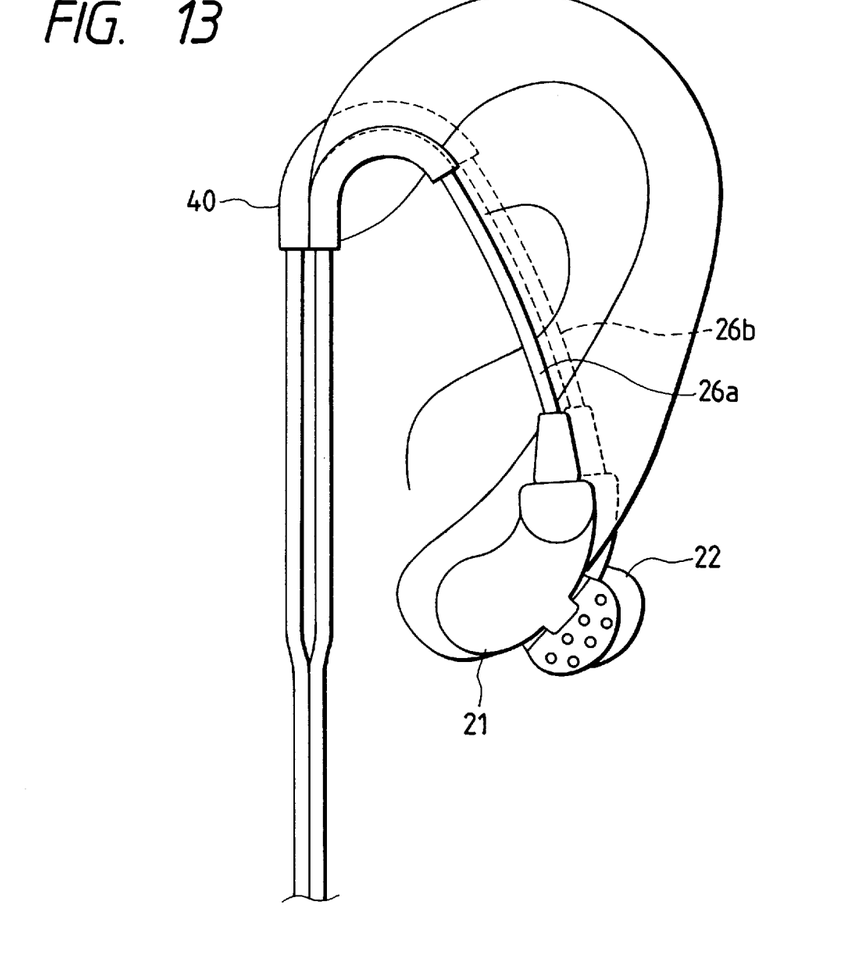
FIG. 13 is a view showing how to use the FIG. 8 probe.

The differences of the second embodiment from the first embodiment will be described. The lead wire 26a and the lead wire 26b are led out of the first housing 21 and the second housing 22, respectively. As shown, in FIG. 13, the lead wires 26a and 26b are inserted into a wire holder 40 at a predetermined length thereof measured from the first housing 21 and the second housing 22. The wire holder 40 consists of two tubes; one end of the holder 40 is separated into two tubes, while the other end is bonded together. The wire holder 40 is bent as shown in FIG. 13. When the probe is attached to the earlobe, the bent holder is put on the earlobe.

Figure 11A:
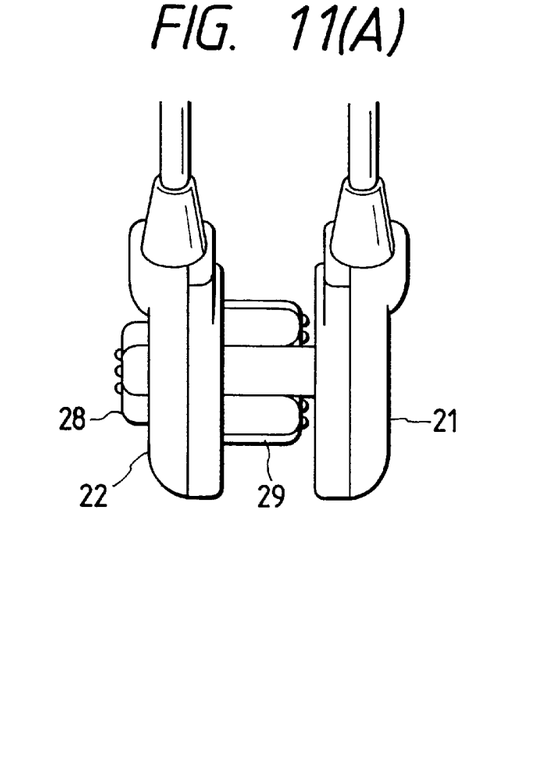
FIGS. 11(A) and FIG. 11(B) are views for explaining the operation of the FIG. 8 probe.
Figure 11B:
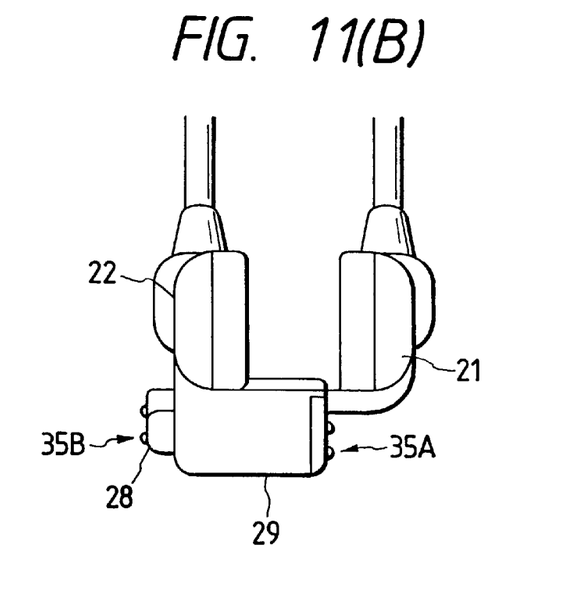
Figure 12:
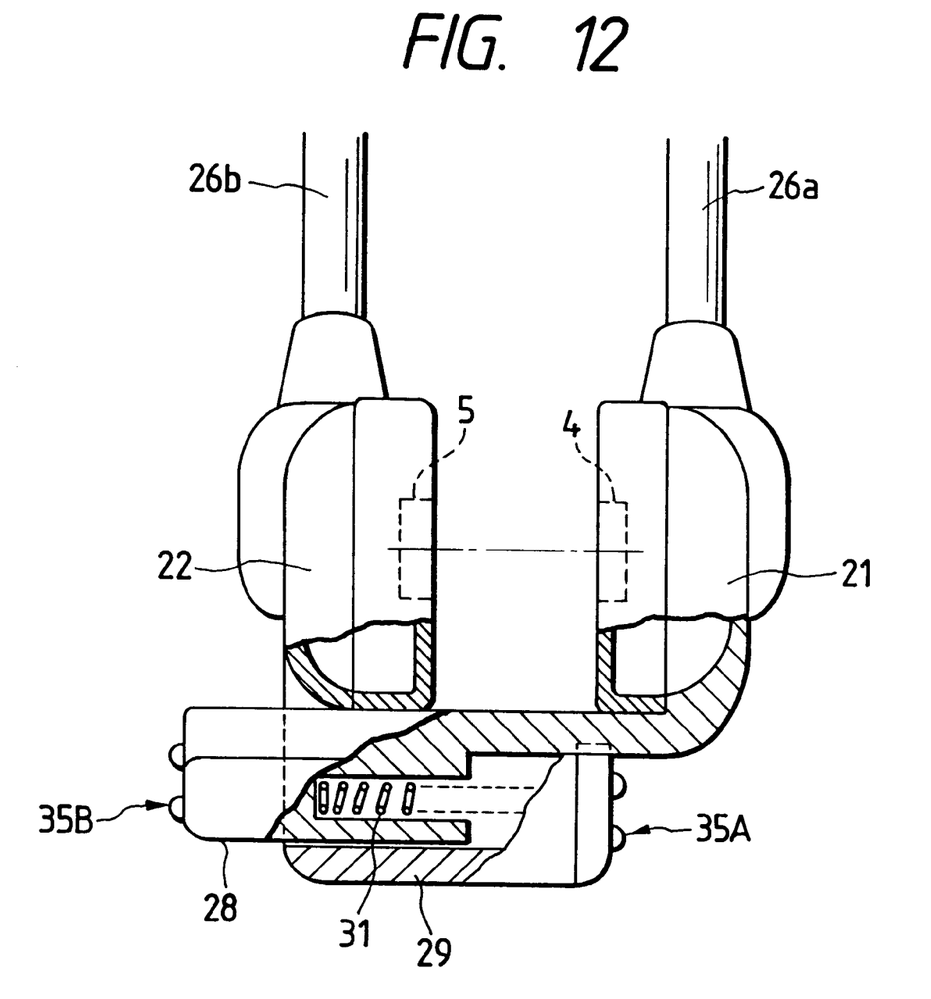
FIG. 12 is another view for explaining the operation of the FIG. 8 probe.

How to use the probe will be described. An operator pinches the pair of knobs 35A and 35B to make a mutual approach of those knobs. As a result, the slide assembly 28 slidably moves with respect to the slide holder 29, and the first housing 21 and the second housing 22 move away from each other, while being parallel to each other. FIG. 11 (A) is a front view showing a state of the probe where the first housing and the second housing are separated from each other. FIG. 11(B) is a plan view showing the same. FIG. 12 is an enlarged view, partly broken, showing the probe illustrated in FIG. 11(B). The operator attaches the probe to an earlobe of a subject; the earlobe is set between the first housing 21 and the second housing 22; gradually loosens his holding of the knobs 35A and 35B and detaches his fingers from the probe; and the earlobe is brought, by the spring (31) force, into close contact with the first optical-element holder 21a and the second optical-element holder 22a, viz., it is compressed between the first housing 21 and the second housing 22.

The operator moves the probe in a state that the lead wire 26a and the lead wire 26b touch the obverse and reverse sides of the earlobe, and places the wire holder 40 of the probe at the upper neck of the earlobe. In this state, the lead wires 26a and 26b are firmly held, and a reduced force is applied from the lead wires 26a and 26b onto the first housing 21 and the second housing 22. The earlobe is firmly set to the earlobe. As shown in FIG. 12, the orientations of the optical axes of the light emitting element 4 and the photo sensing element 5 are invariable even if the earlobe thickness is changed.

In this embodiment, the lead wires 26a and 26b are slidably movable when a certain measure of force is applied to the wire holder 40 so as to adjust their length measured from the first housing 21 and the second housing 22.

In this embodiment, the light emitting element 4 and the photo sensing element 5 are disposed in opposition to each other being supported with the first and second housings to detect a transmitted light through living tissue from the light emitting element 4 to the photo sensing element 5. However, it is capable that both the light emitting element and photo sensing element are disposed on either the first or second housing to detect reflected light reflecting from living tissue by the photo sensing element. Further, the present invention may be applied as not only an oximeter probe but a probe for measuring light absorption constituents in blood generally. In addition, the structure of the movable mechanism for gripping patient's tissue can be applied to 1 sensor for detecting a physiological signal, like an electrode, by disposing an electrode element on an inside surface of a housing.

When a first probe of the present invention is used, the pair of housings may be attached to a finger of a patient in a simple manner. In this case, the biomedical tissue is held between the paired housings in a state that the housings are parallel to each other. Therefore, the probe can reliably be attached to the finger irrespective of the thickness of the finger. Further, it is noted that the light emitting element and the photo sensing element are placed in a parallel state. Therefore, the orientations of the optical axes are invariable, thereby ensuring a stable measurement.

In a second probe of the present invention, the movable mechanism is arranged to form a gap so as to allow one of the pair of housings to be tiltable with respect to the other. With this structural feature, the housings may be brought into close contact with the tip of the finger. Once the probe is set to the finger, the probe, or the housings thereof, is not open unless the knobs are not pressed. Therefore, if the finger is moved in a state that it is nipped between the housings, the probe is not moved and it is hard to off.

In a third probe of the present invention, the lead wires are respectively led out of the ends of the pair of housings, and when the pair of housings are attached to an earlobe of the subject, the wire holder is put on the earlobe and the lead wires are laid along the observe and reverse side of the earlobe. Therefore, the probe can reliably be set to the earlobe.

What is claimed is:

1. A probe for use in emitting light through a patient tissue to measure blood constituents comprising:

a first housing;

a second housing;

a light emitting element disposed on one of said first and second housings;

a photo sensing element for sensing light emitted from said light emitting element, said photo sensing element being disposed on another of said first and second housings;

a movable mechanism having a pair of knobs, said movable mechanism being operable such that when said paired knobs are moved to each other, said movable mechanism moves said housings apart from each other in a state that said housings remain parallel to each other, and when said paired knobs are moved apart from each other, said movable mechanism moves said housings toward each other; and an elastic member for urging said pair of knobs to be separated from each other.

2. The probe according to claim 1, said movable mechanism is arranged to form a gap so as to allow one of said pair of housings to be tiltable with respect to the other.

3. The probe according to claim 1, further comprising:

lead wires for connecting said light emitting element and said photo sensing element to a process device, wherein said light emitting element and said photo sensing element are supported by said first and second housings so as to be disposed in opposition to each other, and wherein said lead wires connected to said light emitting element and said photo sensing element are respectively led out of the ends of said pair of housings, said probe further including a wire holder having two tubes through which said lead wires are inserted respectively, said tubes being separated from each other at one end of said wire holder while said tubes being bonded together at the other end, and when said pair of housings are adapted to be attached to a subject, said wire holder is adapted to be put on the subject and said lead wires are adapted to be laid along the obverse and reverse side of the subject.

4. The probe according to claim 1, wherein an axis of said photo sensing element and an axis of said light emitting element are substantially coincided with each other.

5. A sensor including a pair of housings for gripping patient's tissue, having a physiological signal detecting element on an inside surface of one of said housings comprising:

a movable mechanism having a pair of knobs, said movable mechanism being operable so that when said paired knobs are moved to each other, said movable mechanism moves said housings apart from each other in a state that said housings remain parallel to each other, and when said paired knobs are moved away from each other, said movable mechanism moves said housings toward each other; and an elastic member for urging said pair of knobs to be separated from each other.

6. The sensor according to claim 5, wherein said mechanism is arranged to form a gap so as to allow one of said of housings to be tiltable with respect to the other.

* * * * *